United States Patent [19]
Maki, Jr.

[11] Patent Number: 6,070,465
[45] Date of Patent: Jun. 6, 2000

[54] FREE WATER MEASUREMENT APPARATUS AND METHOD THEREOF

[75] Inventor: Voldi E. Maki, Jr., Austin, Tex.

[73] Assignee: Dresser Industries, Houston, Tex.

[21] Appl. No.: 09/138,724

[22] Filed: Aug. 24, 1998

[51] Int. Cl.[7] .......................... G01N 29/04; G01N 29/18
[52] U.S. Cl. ................... 73/594; 73/597; 73/803
[58] Field of Search .................. 73/597, 594, 590, 73/803, 596

[56] References Cited

U.S. PATENT DOCUMENTS

| | | | |
|---|---|---|---|
| 4,019,576 | 4/1977 | Finch | 166/250 |
| 4,259,868 | 4/1981 | Rao et al. | 73/597 |
| 5,412,990 | 5/1995 | D'Angelo et al. | 73/597 |
| 5,487,300 | 1/1996 | Brackett et al. | 73/61.59 |
| 5,567,765 | 10/1996 | Rao et al. | 73/594 |
| 5,741,971 | 4/1998 | Lacy | 73/597 |

*Primary Examiner*—Helen C. Kwok
*Attorney, Agent, or Firm*—Carlos A. Torres; Patrick H. McCollum

[57] ABSTRACT

An free water measurement apparatus and device for measuring the free water that separates from the cement slurry as a matter of time during curing. There is also provided an apparatus and method for measuring the free water that separates from the cement slurry under the temperature and pressure conditions the cement slurry will encounter in the well-bore of an oil and gas well. The apparatus and method provided may further measure the compressive strength measurement of the cement slurry as it is cured.

19 Claims, 4 Drawing Sheets

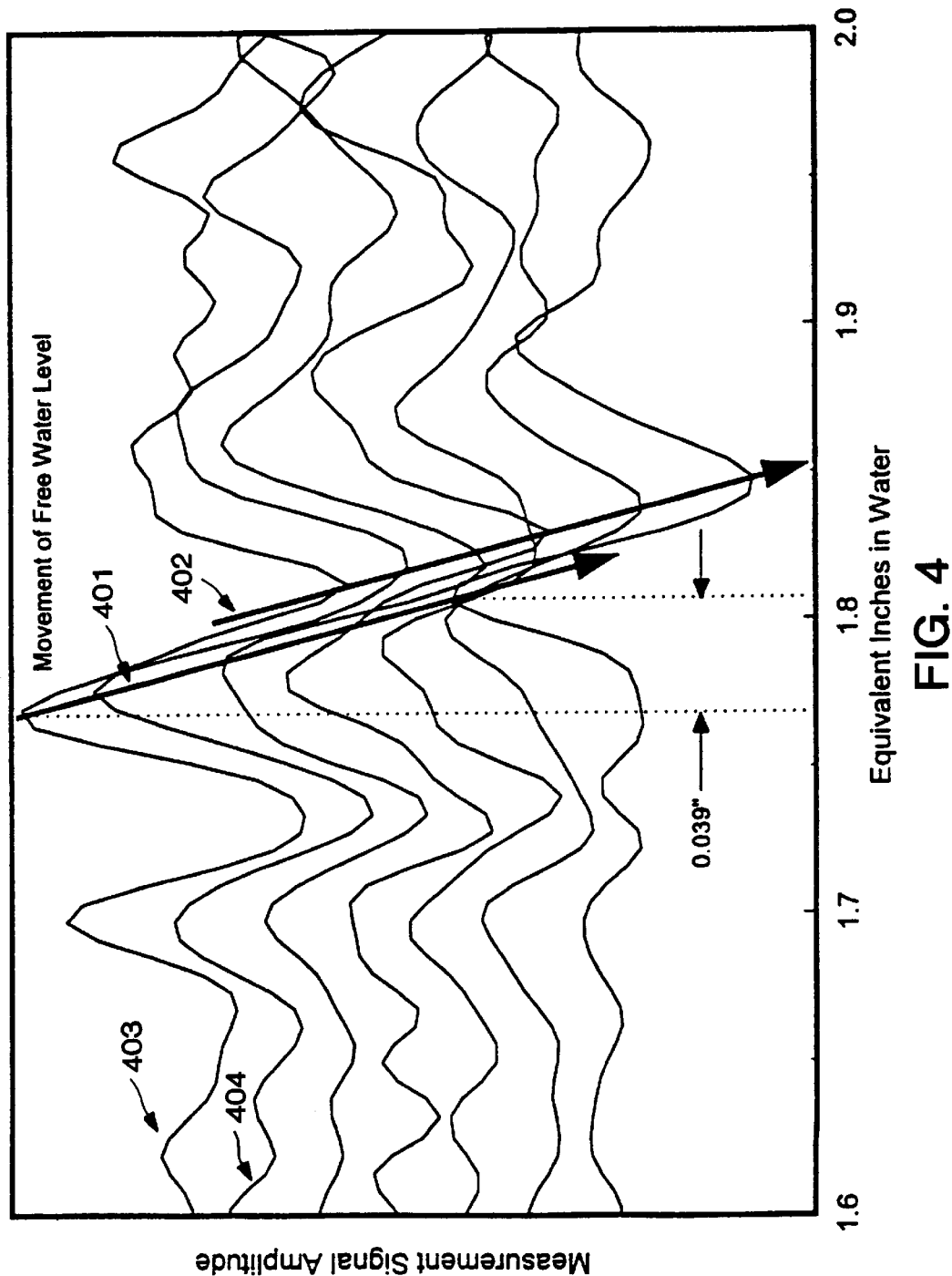

FREE WATER MEASUREMENT APPARATUS AND METHOD THEREOF

TECHNICAL FIELD

The present invention relates in general to a free water measurement apparatus and method measuring the free water that separates from a cement slurry during curing, and in particular, an apparatus and method measuring the free water that separates from the cement slurry as it cures over time and measuring the free water that separates from the cement slurry as it cures under the temperature and pressure conditions the cement slurry will encounter in the well-bore of an oil and gas well. The present invention may further be utilized for measuring the compressive strength measurement of the cement slurry as it cures.

BACKGROUND INFORMATION

An amount of water will separate from a cement slurry during the curing (or setting) process. This amount of water produced from the cement slurry is referred to as the free water. Historically, in order to determine the free water amount for a particular cement slurry, a standard American Petroleum Institute (API) test well known in the art has been utilized. During this API test, a 9.4 inch sample of the cement slurry is placed into a 1.5 inch diameter column. As the cement slurry sets, a small amount of water separates from the cement slurry and accumulates on the top of the column. After two hours, the amount of water is measured. This is the free water, and is expected in small amounts. An excessive amount is a symptom of poor cement and a poor cement slurry.

It is apparent that there are shortcomings with the API test. The free water measured is only determined after two hours; thus, this test is not informative as to how the free water disassociated from the cement slurry over time. While it is possible to run multiple samples, such a procedure would be lengthy and cumbersome. Moreover, this test for free water is performed at room temperature and at atmospheric pressure, rather than at the actual temperatures and pressures encountered in the well-bore environment. Since the rate at which a cement slurry cures is generally dependant upon temperature and pressure, the free water test is not performed under the conditions that will be encountered during actual use.

The advantages of testing cement and cement slurry over time under the well-bore conditions is recognized in the art. The standard device for testing cement at well-bore temperature and pressure is the UCA, which was originally introduced by Halliburton. The UCA was disclosed in U.S. Pat. No. 4,259,868 issued to Rao, et al. ("Rao") and teaches a method and apparatus for nondestructive testing of cement as a function of time and under temperature and pressure control. However, the UCA does not measure the free water of the cement slurry. The UCA design utilized two transducers in the pitch-catch mode. This mode of operation would allow the measurement of the average sound velocity of the material and attenuation of the material in the path of the acoustic signal. It could not, however, allow for the detection of layering in the material in the acoustic path. Since the free water forms as a layer above the cement slurry and cement, the design of the UCA could not measure the free water.

Therefore, there is a need in the art for an apparatus and method for measuring the free water as a function of time as it separates from a cement slurry and for measuring the free water as it separates from the cement slurry during curing under the temperature and pressure conditions the cement will encounter in the well-bore of an oil and gas well.

SUMMARY OF THE INVENTION

The aforementioned needs are addressed by the present invention. Accordingly there is provided an apparatus and method for measuring the free water that separates from the cement slurry as a matter of time during curing. There is further provided an apparatus and method for measuring the free water that separates from the cement slurry under the temperature and pressure conditions the cement slurry will encounter in the well-bore of an oil and gas well. The apparatus and method provided may further measure the compressive strength measurement of the cement slurry as it cures.

The apparatus and method described herein is a modification of the UCA device (which, as noted above is disclosed in Rao) to achieve the capability of measuring the free water. U.S. Pat. No. 4,259,868 issued to Rao et al. is hereby incorporated by reference herein.

The present invention utilizes a single transducer operated in the pulse/echo mode. The transducer produces an acoustic pulse, which propagates through the material in the enclosed cell. With no layering, the pulse program propagates through the cement slurry, is reflected by the bottom plug of the cell, and is then reflected back to the transducer. If there is any layering, the interfaces between each material reflect some of the acoustic signal back to the transducer.

The present invention has the further advantage of being able to measure the compressive strength of the cement at the same time it measures the free water.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 4 illustrates, in graphical form, a series of difference signals recorded in accordance with the present invention.

DETAILED DESCRIPTION

Figure 1:
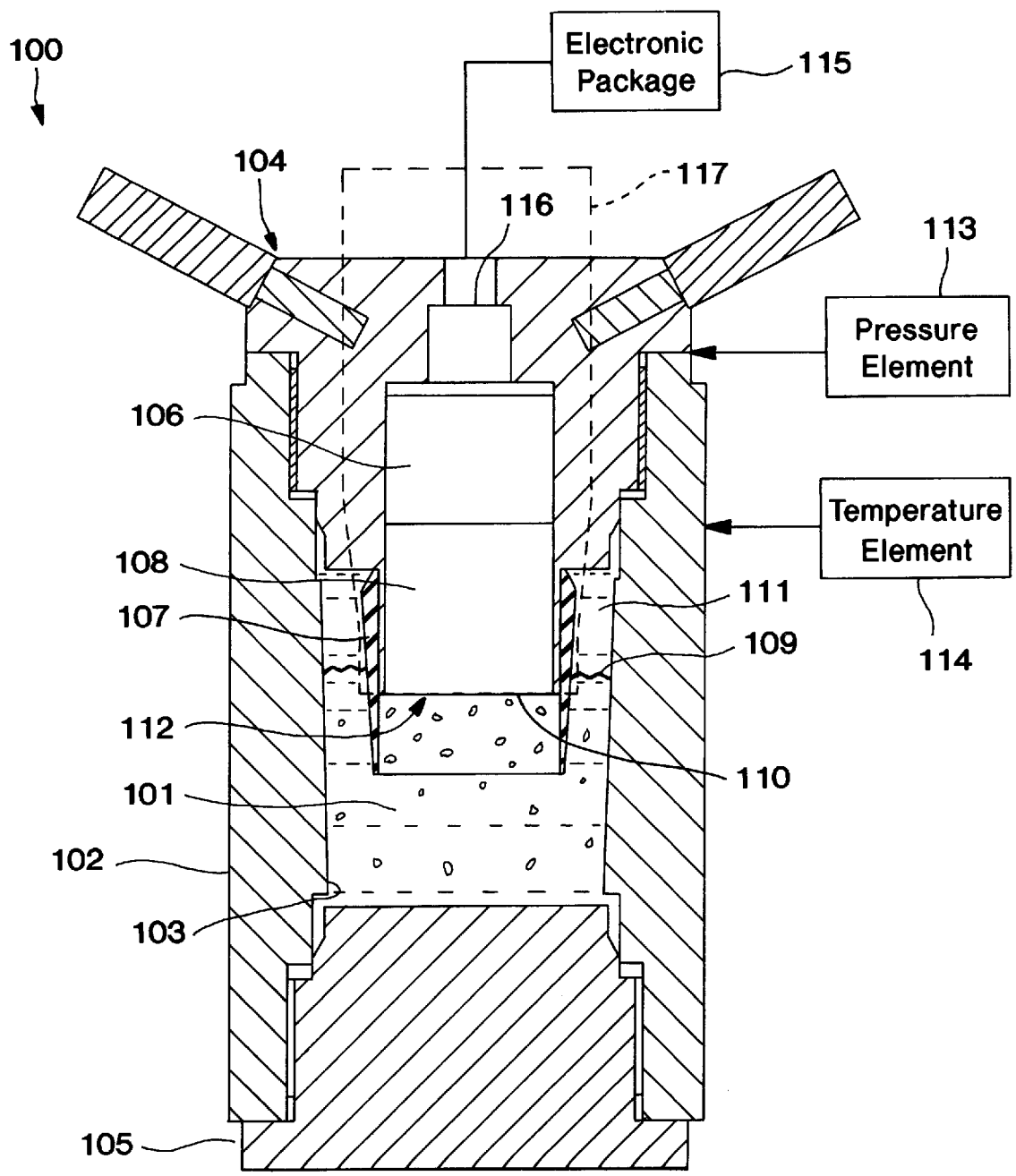
FIG. 1 illustrates, in block diagram form, the free water measurement apparatus for measuring in accordance with an embodiment of the present invention.

The present invention provides an apparatus and method for measuring the free water that is produced from a cement slurry. A cement slurry is placed in a free water measurement apparatus and allowed to cure. Within the cell, the cement slurry forms a column. Because the cell is temperature and pressure controlled, these can be adjusted to subject the cement slurry to the conditions it would experience in the well-bore of an oil and gas well. As the curing takes place within the cell, the free water accumulates at the surface of the cement column and is detected by a transducer. The amount of free water is measurable by the timing of the acoustic signal. Since the acoustic device does not affect the curing of the cement or the rate of free water accumulation, this device is able to measure the free water accumulation over time.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

Refer now to the drawings wherein depicted elements are not necessarily shown to scale and wherein like or similar elements are designated by the same reference numeral through the several views.

Refer first to FIG. 1 which shows a free water measurement apparatus 100 in accordance with an embodiment of the present invention. The free water measurement apparatus 100 has an enclosed cell, such as a pressure vessel 102, in which a cement slurry 101 (also referred to as a cement sample) may be received. The pressure vessel 102 may be a cylinder such as shown in FIG. 1 and also shown in Rao (FIG. 6, item 64). Pressure vessel 102 has an inner wall 103.

Pressure vessel 102 also has a top plug 104 and bottom plug 105. An acoustic device 117 is received in the pressure vessel 102. The acoustic device 17 utilizes a pulse echo measurement to measure the thickness of the layer of free water formed on top of the cement slurry 101. The acoustic device has a transducer 106 that can be positioned in the top plug 104 and a delay line 108 attached to the transducer. A confinement sleeve, such as rubber confinement sleeve 107, is attached to the top plug 104 and surrounds and extends below the delay line 108. The cement slurry 101 is filled in the pressure vessel 102 to a top surface 109 of the cement slurry 101. The top surface 109 of the cement slurry 101 is such that when the top plug 104 is received into the pressure vessel 102, the top surface 109 of the cement slurry 101 is above the bottom face 110 of the delay line 108.

As the top plug 104 is received into the pressure vessel 102, the rubber confinement sleeve 107 is completely filled with cement slurry 101 below the bottom face 110 of delay line 108. It is at the interface at the bottom face 110 of delay line 108 and the cement slurry 101 inside the rubber confinement sleeve 107 where the free water 112 accumulates and is measured.

The pressurized cell 102 is pressurized with water 111. The water 111 is added to the top surface 109 of the cement slurry 101 such that the water 111 does not contaminate the cement slurry 101 in the pressurized cell 102.

A pressure element 113 and a temperature element 114 can be utilized to control the temperature and pressure of the cement slurry 101. For example, Rao discloses the use of a temperature and pressure autoclave provided with a pressure vessel and a temperature element such as a heater coil to maintain a predetermined temperature and pressure on the cement sample throughout the test. Rao utilizes pressure and temperature control mechanisms (shown therein in FIG. 6, item 63). The system (shown in Rao, FIG. 6, item 61) is part of the temperature and pressure control electronics. In the present invention, this system may also include program codes, which control the transducer 106 and measure compressive strength. The present invention also has an electronic package 115, which is attached to the transducer 106 by an electrical connector, such as a high pressure electrical connector 116, in top plug 104. The electronic package 115 will be used to measure free water 112 accumulation. The electronic package 115 may also be capable of measuring the compressive strength in a manner similar to the method described in Rao.

During operation, the transducer 106 in the top plug 104 sends an acoustic signal (a soundwave) through the cement slurry 101 where it is reflected from the bottom plug 105 and travels back to the transducer 106. As the acoustic pulse travels away from the transducer 106 it may be referred to as the transmit pulse. As the acoustic pulse returns to the transducer 106 it may be referred to as the echo pulse. The delay line 108 isolates the transducer 106 from the cement slurry 101. This delay line 108 allows the transducer 106 to become quiet after it generates the acoustic measurement pulse. As the free water 112 accumulates inside rubber confinement sleeve 107 at the bottom face 110 of the delay line 108, the reflection from the interface between the free water 112 and the cement slurry 101 is measured using the acoustic signal. This gives the level of the free water 112 above the cement slurry 101. This level of free water 112 may be used to estimate the comparable measurement obtained in the standard API test for free water. The free water 112 height is then used to determine the height of the cement slurry 101 column below the delay line so that after looking at the signal reflected from the bottom plug 105, the sound velocity in the cement slurry 101 may be calculated. From the sound velocity, the cement compressive strength may be calculated. This process results in both a free water measurement and a compressive strength measurement.

The received echo is received by transducer 106, and transducer 106 sends a recorded acoustic signal representative of the received echo to the electronic package 115. This received acoustic signal sent by the transducer 106 to the electronic package 115 is analog, although the recorded acoustic signal is digital. The electronic package 115 then processes the received acoustic signal to determine the free water 112 and cement slurry 101 measurements. It should be understood that the actual process of transmitting a transmit pulse and receiving a received echo, generating a recorded acoustic signal representative of the received echo, and processing the recorded acoustic signal (by electronic package 115) are well known in the art. Such an apparatus and method is described in U.S. Pat. No. 5,044,462 issued to Maki, which is incorporated by reference herein.

Figure 2:
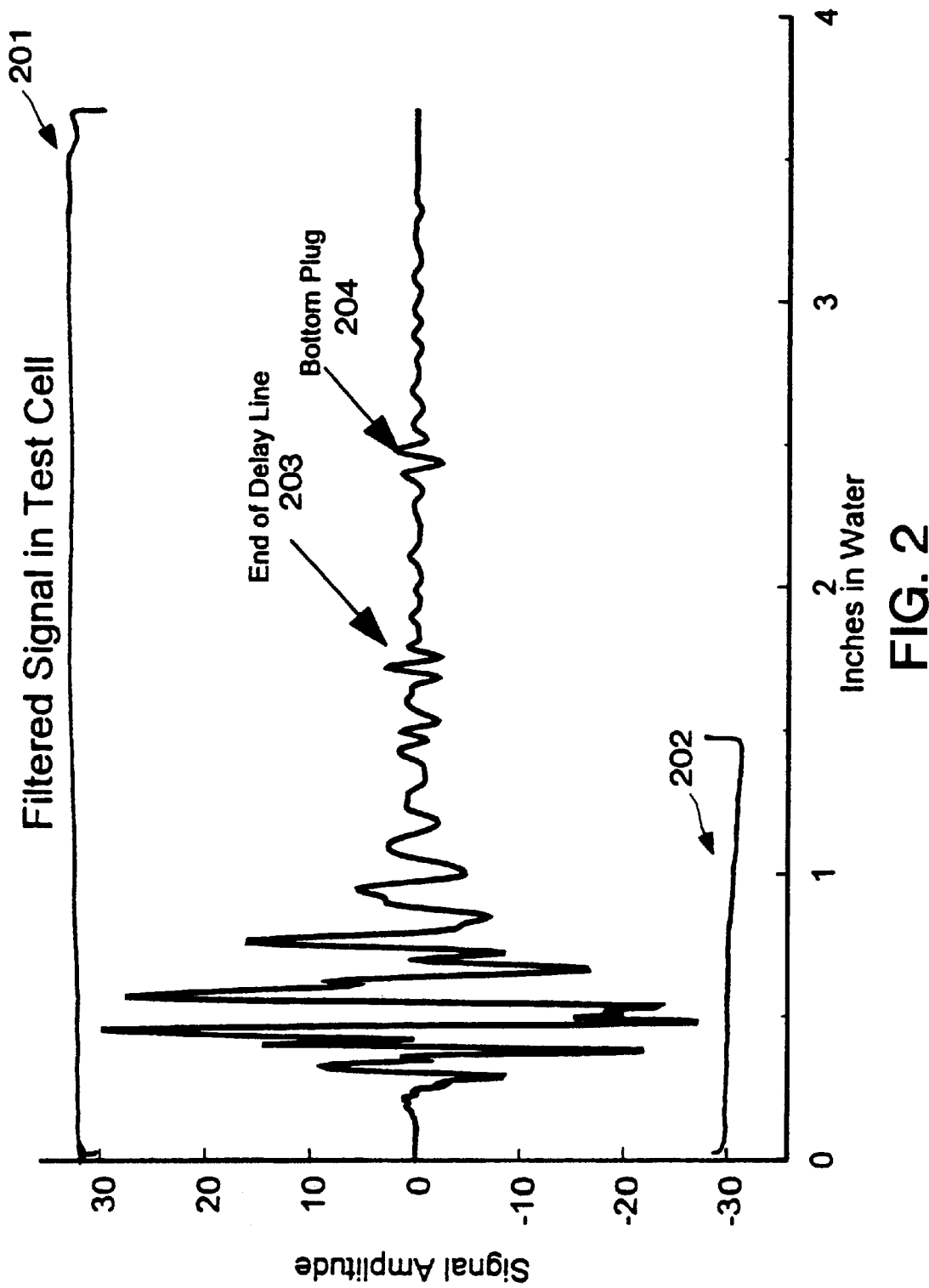
FIG. 2 illustrates, in graphical form, an acoustic signal recorded in accordance with the present invention.

FIG. 2 shows a typical acoustic signal 201 recorded in accordance with the present invention. For this test, a small cylindrical pressure cell 102 was used having an inner wall 103 with a 2.5 inch diameter; accordingly, the cement slurry 101 inside the pressure vessel 102 also had a 2.5 inches diameter. The top surface 109 of the cement slurry 101 was about 1 inch in height, which was about ¼ inch above the bottom face 110 of delay line 108. From these dimensions, the pressure cell 102 had 0.75 inches of cement slurry 101 between the end of delay line 108 and the bottom plug 105.

The received acoustic signal 201 (a received echo) appears as shown in FIG. 2 after filtering by the electronic package 115 to remove noise. The time scale is shown translated to equivalent distance in water using a sound velocity of 1500 meters per second. The very large acoustic signal 202 lasting for about 1.5 inches or 50 microseconds is the residual signal in the transducer 106 after it generates the acoustic pulse. The acoustic signal 203 at the interface between the delay line 108 and the top of the cement slurry 101 is at the location shown. The acoustic signal 204 from the bottom plug 105 is shown much later at about 2.3 inches. The acoustic signal 204 from the bottom plug 105 is opposite in phase from the acoustic signal 203 at the end of the delay line 108. Since the reflection signal is due to a change in impedance, an increase in impedance, such as the bottom plug 105, will be opposite in phase from the acoustic signal 203 at the end of the delay line 108 because water has a lower impedance than the plastic of the bottom plug 105.

As the free water 112 is formed, a second received acoustic signal (a second received echo) will appear, superimposed upon the first received acoustic signal 201. The second acoustic signal is the reflection from the interface between the free water 112 and the cement slurry 101, and it will be opposite in phase. Since the second acoustic signal is very low in amplitude and initially appears less than one wavelength away from the first, it is almost impossible to detect without using some type of processing. Because the electronic package 115 digitizes the waveform, the electronic package 115 may perform the signal processing. Since the free water 112 is increasing during the experiment, the second acoustic signal will move slowly away from the first acoustic signal 201 at the end of the delay line with each successive measurement. The change in the waveform with time may be used to separate it from the reflection at end of the delay line 108, which is much larger, but does not change with time. Taking the difference between two waveforms with a one-minute separation results in the difference signal 302 shown in FIG. 3.

Figure 3:
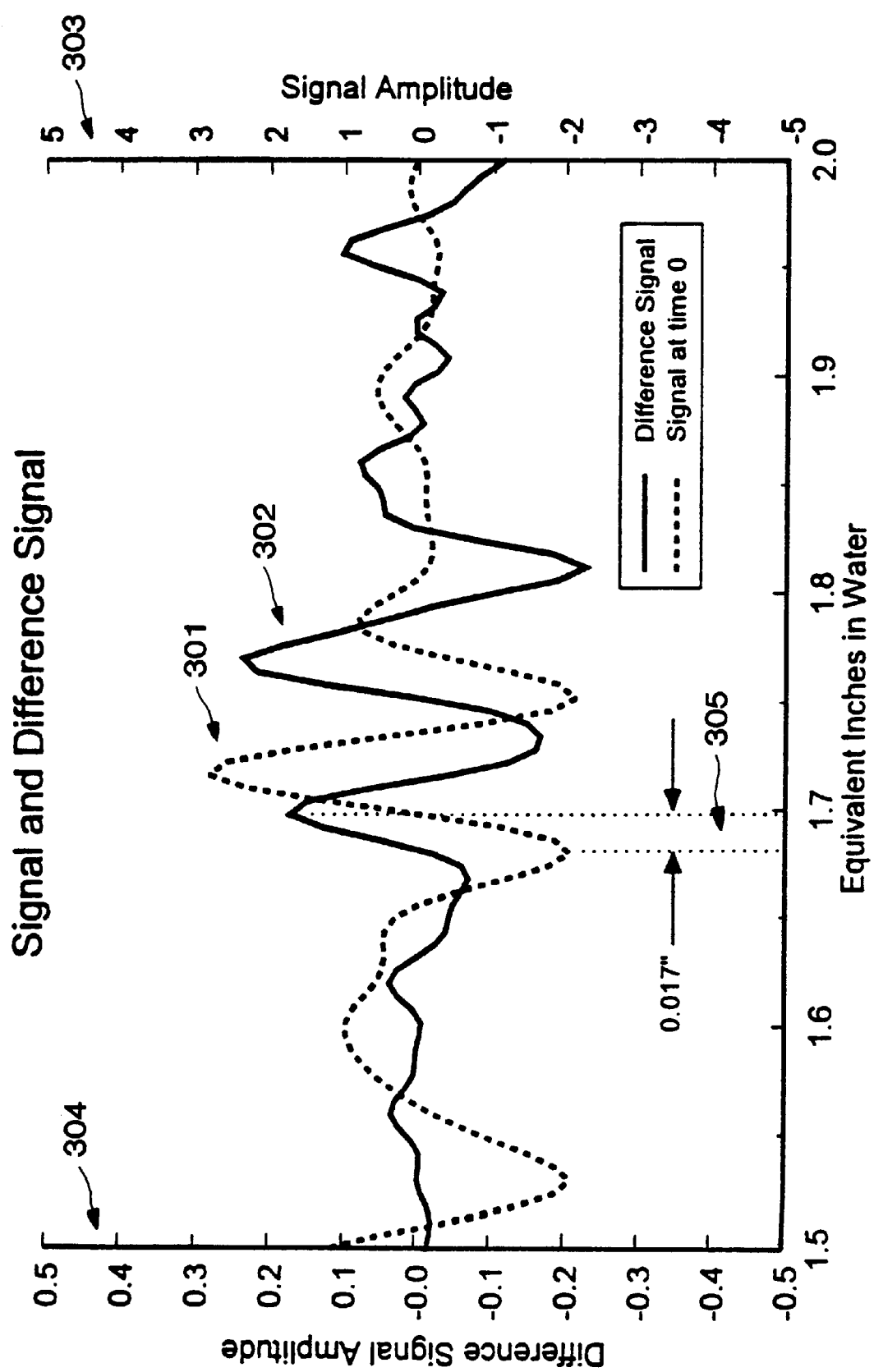
FIG. 3 illustrates, in graphical form, an acoustic signal and difference signal recorded in accordance with the present invention.

FIG. 3 shows an acoustic signal and difference signal recorded in accordance with the present invention. The dashed line shows the first acoustic signal 301, showing the location of the end of the delay line 108 as a large signal. The scale of the first acoustic signal is shown on the right hand axis 303 (scale from −5 to 5). In this case, first acoustic signal 301 is the same acoustic signal 201 as shown in FIG. 2. The solid line is the difference signal 302. The difference signal 302 is the difference between the first acoustic signal 301 and the second acoustic signal (not pictured). The scale of the difference signal 302 is shown on the left hand axis (scale −0.5 to 0.5) In FIG. 3, the amplitude scale for first acoustic signal 301 is 10 times larger than the scale for the difference signal 302 and that it is opposite in phase to that from the end of the delay line. The difference in the time of arrival 305 is equivalent to 0.017 inches. Because of the time required to set up the pressurized vessel 102 after the cement slurry 101 is added, a small amount of free water already exists in this first measurement.

FIG. 4 shows a series of difference signals recorded in accordance with the present invention. By sampling the pressurized vessel 102 once per minute and taking the difference between adjacent samples, the graph in FIG. 4 was obtained. Each trace beginning at the top is the difference signal taken one minute later than the trace above it. For instance, second difference signal 404 was taken one minute after first difference signal 403. By tracking the peaks or valleys, the movement of the free water 112 to cement slurry 101 interface may be located as the experiment progresses. This change in distance added to the initial distance shown in FIG. 3 shows the total free water 112 above the cement slurry 101. There will be some noise in the difference signal due to the movement of fines in the free water 112 producing some small changes in the reflection amplitude at the delay line 108. This change in signal will slightly modify the reflection from the free water 112 to cement slurry 101 interface. Using the highest amplitude part of the difference signal proves to be the most reliable for measuring the fluid level. The arrows 401 and 402 show that over the period of eight minutes, the free water increased by 0.039 inches. The total amount of free water is 0.017 plus 0.039 or 0.056 inches. Once the cement slurry has cured, the thickness of the fluid column may be measured with a caliper to verify the accuracy of the acoustic measurements.

Although the present invention and its advantages have been described in detail, it should be understood that various changes, substitutions and alterations can be made herein without departing from the spirit and scope of the invention as defined by the appended claims.

What is claimed is:

1. A free water measurement apparatus comprising:
    (a) a cell for receiving a cement slurry; and
    (b) an acoustic device having a transducer and a delay line the acoustic device operable to measure a free water formed from the cement slurry.

2. The free water measurement apparatus of claim 1, further comprising a heating element operable to heat the cement slurry.

3. The free water measurement apparatus of claim 1, further comprising a pressurizing element operable to pressurize the cell.

4. The free water measurement apparatus of claim 1, further comprising
    a confinement sleeve operable to confine a first portion of the cement slurry.

5. The free water measurement apparatus of claim 4, further comprising a heating element operable to heat the cement slurry and a pressurizing element operable to pressurize the cell.

6. The free water measurement apparatus of claim 4, wherein:
    (b) the transducer is operable for transmitting a first transmit pulse and a second transmit pulse;
    (c) the transducer is operable for receiving a first echo of the first transmit pulse and a second echo of the second transmit pulse;
    (d) an electronic package for processing the first echo and second echo.

7. The free water measurement apparatus of claim 6, wherein the electronic package is operable to process the first echo and the second echo to measure a layer of the free water on a top side of the first portion of the cement slurry and to measure a compressive strength of the cement slurry.

8. The free water measurement apparatus of claim 7, further comprising a heating element operable to heat the cement slurry and a pressurizing element operable to pressurize the cell.

9. A method for measuring free water from a cement slurry, comprising the steps of:
    (a) receiving the cement slurry into a cell;
    (b) transmitting a first transmit pulse through the cement slurry;
    (c) receiving a first echo pulse in response to the first transmit pulse;
    (d) processing the first echo pulse to measure the free water from the cement slurry.

10. The method for measuring free water from a cement slurry of claim 9, further comprising the steps of pressurizing the cell.

11. The method for measuring free water from a cement slurry of claim 9, further comprising the steps of heating the cement slurry.

12. The method for measuring free water from a cement slurry of claim 9, further comprising the step of
 (a) transmitting a second transmit pulse through the cement slurry;
 (b) receiving a second echo pulse in response to the second transmit pulse;
 (c) processing the first echo pulse and the second echo pulse to measure the free water from the cement slurry.

13. The method for measuring free water from a cement slurry of claim 12, further comprising the steps of processing the first echo pulse and the second echo pulse to measure a compressive strength of the cement slurry.

14. The method for measuring free water from a cement slurry of claim 13, further comprising the steps of pressurizing the cell and heating the cement slurry.

15. An apparatus for measuring the free water separated from a cement slurry, comprising:
 (a) a pressurized cell for receiving the cement slurry;
 (b) a pressurizing element for pressurizing the pressurize cell;
 (c) a heating element for heating the cement slurry;
 (d) a transducer for transmitting and receiving a plurality of acoustic signals; and
 (e) an electronic package for processing the acoustic signals operable to measure the free water.

16. The apparatus of claim 15, further comprising a containment sleeve inside the pressurized cell.

17. The apparatus of claim 15, further comprising the electronic package operable to to measure a compressive strength of the cement slurry.

18. A free water measurement apparatus comprising:
 (a) a cell for receiving a cement slurry;
 (b) a confinement sleeve operable to confine a first portion of the cement slurry; and
 (c) an acoustic device having a transducer and a delay line, wherein the transducer is operable to measure a layer of free water on a top side of the first portion of the cement slurry.

19. The apparatus of claim 18, further comprising a pressure element and a temperature element operable to control the temperature and pressure of the cement slurry.

* * * * *